United States Patent [19]
Choi et al.

[11] Patent Number: 5,616,472
[45] Date of Patent: Apr. 1, 1997

[54] PROCESS FOR PRODUCING MONOCLONAL ANTIBODIES AGAINST HUMAN T CELL RECEPTOR ELEMENTS USING RECOMBINANT DNA VECTORS, AND CELLS TRANSFECTED THEREBY

[75] Inventors: Yongwon Choi; John Kappler; Philippa Marrack, all of Denver, Colo.

[73] Assignee: National Jewish Center for Immunology and Respiratory Medicine, Denver, Colo.

[21] Appl. No.: 278,629

[22] Filed: Jul. 21, 1994

Related U.S. Application Data

[63] Continuation of Ser. No. 565,439, Aug. 9, 1990, abandoned.
[51] Int. Cl.$^6$ .............. C12P 21/04; C12P 21/06; C12N 15/00; C12N 5/00
[52] U.S. Cl. .............. 435/69.1; 435/69.6; 435/172.3; 435/320.1; 435/334; 435/343.2
[58] Field of Search .............. 530/388.75, 388.25; 435/69.1, 320.1

[56] References Cited

U.S. PATENT DOCUMENTS

| 5,189,147 | 2/1993 | Saito | 530/387.9 |
|---|---|---|---|
| 5,223,426 | 6/1993 | Skibbens | 435/240.27 |

FOREIGN PATENT DOCUMENTS

WO9006758  6/1990  WIPO.

OTHER PUBLICATIONS

Blackman et al Cell 47:439, 1986.
Yague et al Cell 42:81–87, 1985.
Dembic et al. Nature 320:232, 1986.
Choi et al PNAS 86:8941, 1989.
Goding, in Monoclonal Antibodies: Principles and Practice p. 61, 1983.
Kamarck et al PNAS 84:5350. 1987.
Toyanaga et al Ann. Rev. Immunol 5:585–620. 1987.
Kappler et al. Cell 49:263. 1987.
Toyanaga et al. Ann. Rev. Immol 5:585, 1987.
Kimura et al Eur. J. Immunol. 17: 375, 1987.
Gross et al. PNAS 86: 10024, 1989.
Friedman et al., J. Exp. Med. 174: 891–900 (10–91).
Bigler et al., J. Exp. Med. 158: 1000–1005 (1983).
Carrel et al., Eur. J. Immunol. 16: 649–652 (1986).
Posnett et al., PNAS 83: 7888–7892 (Oct. 1986).
Yssel et al., Eur. J. Immunol. 16: 1187–1193 (1986).
Borst et al., J. Immunol. 139(6): 1952–1959 (Sep. 15, 1987).
Abe and Hodes (1988) J. Immunol. 140:4132.
Babbitt et al. (1985) Nature 317:359.
Bekoff et al. (1987) J. Immunol. 139:3189.
Bjorkman et al. (1987) Nature 329:506
Blackman et al. (1986) Cell 47:349.
Burgert et al. (1989) J. Exp. Med. 170:1887.
Buus et al. (1987) Science 235:1353.
Choi et al. (1989) Proc. Natl. Acad. Sci. USA 86:8941.
Grey et al. (1989) Scientific American 261:56.
Hedrick et al. (1982) Cell 30:141.
Ho et al. (1989) Gene 77:51.
Janeway et al. (1989) Immunol. Rev. 107:61.
Kappler et al. (1987) Cell 49:263.
Kappler et al. (1988) Nature 332:35.
Kappler et al. (1987) Cell 49:273.
Kappler et al. (1989) Science 244:811.
Kohler and Milstein (1975) Nature 256:495.
Kronenberg (1986) Ann. Rev. Immunol. 4:529.
Kubo et al. (1989) J. Immunol. 142:2736.
MacDonald et al. (1988) Nature 332:40.
Male et al. (1987) *Advanced Immunology* J.B. Lippincott Co., Chapters 6–10.
Marrack and Kappler (1988) Immunol. Today 9:308.
Pullen et al. (1988) Nature 335:796.
Saiki et al. (1988) Science 239:487.
Townsend et al. (1986) Cell 44:959.
Toyonaga and Mak (1987) Ann. Rev. Immunol. 5:585.
White et al. (1989) Cell 56:27.
Traunecker et al. (1986) Euro. Journ. of Immunology 16:851–854.
Gascoigne, N.R.J., et al. (1987) Proceedings of the Nat'l Academy of Sciences USA 84:29636–2940.
Kohler, G., et al. (1975) Nature 256:495–497.
Goding (1983) *Monoclonal Antibodies:Principles and Practice*, pp. 1–97 (Academic Press).
Leo et al. (1987) Proc. Natl. Acad. Sci. USA 84:1374–1378.

*Primary Examiner*—Suzanne E. Ziska
*Attorney, Agent, or Firm*—Swanson & Bratschun, LLC

[57] ABSTRACT

Recombinant DNA vectors which express chimeric T cell receptors are disclosed. These chimeric T cell receptors contain one human element, and the rest of the elements are all of the same, non-human animal species, such as a mouse. Of particular interest are chimeras where the human element is Vα or Vβ. The vectors are used to transfect cells which derive from the same non-human animal species as the non-human animal species of the chimera, and the resulting transfectants are used to produce monoclonal antibodies against the human element of the chimera.

8 Claims, 1 Drawing Sheet

PROCESS FOR PRODUCING MONOCLONAL ANTIBODIES AGAINST HUMAN T CELL RECEPTOR ELEMENTS USING RECOMBINANT DNA VECTORS, AND CELLS TRANSFECTED THEREBY

This is a continuation of application(s) Ser. No. 07/565,439 filed on Aug. 9, 1990 now abandoned.

FIELD OF THE INVENTION

This invention relates to the field of immunology. More particularly, it relates to the preparation of chimeric molecules which are useful as cell surface antigens in the generation of antibodies, particularly monoclonal antibodies, to specific components of the repertoire of T cell receptor molecules.

BACKGROUND AND PRIOR ART

In recent years, the mechanism by which mammalian immune systems, such as human and murine systems react to infections, foreign antigens, and to so-called "self antigens" in connection with autoimmune diseases has begun to be established. See, in this regard, Grey, et al., Scientific American 261(5): 56–64 (1989); Male, et al., *Advanced Immunology* (J. P. Lippincott Company, 1987), especially chapters 6 through 10.

Well known, both to the skilled artisan and to the general public is the role of antibodies, sometimes referred to as "immunoglobulin" or the less correct and older "gamma-globulin" in response to infection. Antibodies are protein molecules which are produced by B cells in response to infection. It is well known that these antibodies act to "disable" or to inactivate infectious agents in the course of combating the infection.

In order for antibodies to be produced, however, preceding events must occur which lead to stimulation of the B cells which produce the antibodies. One of the key events involved in the processes leading to antibody production is that of antigen recognition. This aspect of the immune response requires the participation of so-called "T-cells" and is less well known than the antibody response commented on supra.

Briefly, and in outline form, antigen recognition requires interaction of an "antigen presentation cell", a "processed antigen", and a T-cell. See Grey and Male, supra. The "processed antigen" in an infection, is a molecule characteristic of the pathogen which has been treated, i.e., "processed", by other cells which are a part of the immune system. The processed antigen interacts with a receptor on the surface of a presenting cell in a manner not unlike a lock fitting into a key hole or, perhaps more aptly, two pieces of a jigsaw puzzle.

The configuration of the complex of processed antigen and receptor on an antigen presenting cell allows the participation of T-cells. T-cells do not join the complex unless and until the processed antigen has fit into the receptor on the antigen presenting cell. This receptor will hereafter be referred to by its scientific name, the major histocompatibility complex (MHC), or the human leukocyte antigen (HLA). Generally, MHC is used to refer to murine systems, and HLA to humans.

These receptors fall into two classes. MHC-II molecules are involved in most responses to pathogens. In contrast, MHC-I molecules are involved when the pathogen is a virus, or a malignant cell is involved. When MHC-I participation is involved, there is no antibody stimulation; rather, the interaction of MHC-I, processed antigen and T-cell leads to lysis of cells infected with the pathogen.

The foregoing discussion has focused on the events involved in responding to "infection", i.e., the presence of pathogenic foreign material in the organism. Similar mechanisms are involved in autoimmune diseases as well. In these conditions, the organism treats its own molecules as foreign, or as "self-antigens". The same type of complexing occurs as described supra, with an antibody response being mounted against the organism itself. Among the diseases in which this is a factor are rheumatoid arthritis, diabetes, systemic lupus erythromatosus, and others.

The ability of the T-cell to complex with the processed antigen and MHC/HLA complex is dependent on what is referred to as the T-cell antigen receptor, referred to as "TCR" hereafter. The TCR is recognized as a heterodimer, made up of alpha ($\alpha$) and beta ($\beta$) chains. Five variable elements, coded for by germline DNA and known as "V$\alpha$, J$\alpha$, V$\beta$, D$\beta$ and J$\beta$" as well as non-germline encoded amino acids contribute to the TCR. See, in this regard, Marrack et al., Immunol. Today 9: 308–315 (1988); Toyonaga et al., Ann. Rev. Immunol. 5: 585–620 (1987); Davis, Ann. Rev. Immunol. 4: 529–591 (1985); Hendrick et al., Cell 30:141–152 (1982). With respect to the binding of TCR with processed antigen and MHC, see Babbitt et al., Nature 317:359–361 (1985); Buus et al., Science 235: 1353–1358 (1987); Townsend et al., Cell 44: 959–968 (1986); Bjorkman et al., Nature 329: 506–512 (1987).

Generally, both the alpha and beta subunits are involved in recognition of the ligand formed by processed antigen and MHC/HLA molecule. This is not always the case, however, and it has been found that so-called "superantigens" stimulate T-cells with a particular V$\beta$ element, regardless of any other element. See Kappler et al., Cell 49: 273–280 (1987); Kappler et al., Cell 49: 263–271 (1987); MacDonald et al., Nature 332: 40–45 (1988); Pullen et al., Nature 335: 795–801 (1988); Kappler et al., Nature 332: 35–40 (1988); Abe et al., J. Immunol. 140: 4132–4138 (1988); White et al., Cell 56: 27–35 (1989); Janeway et al., Immunol. Rev. 107: 61–88 (1989); Berkoff et al., J. Immunol. 139: 3189–3194 (1988), and Kappler et al., Science 244: 811–813 (1989).

The "superantigens" mentioned supra, while generally stimulating T-cells as long as they possess a V$\beta$ element, are somewhat specific in terms of the particular form of the V$\beta$ moiety which is present on the stimulated T cell.

The V$\beta$ element may be any of a number of different members of a related family of such elements. Different members of the family have different effects. See, in this regard Choi et al., Proc. Natl. Acad. Sci. USA 86: 8941–8945 (1989), which showed that T-cells bearing human V$\beta$ 13.2 respond to antigen SEC 2, while closely related V$\beta$ 13.1 does not induce that type of result.

Study of the different members of the V$\beta$ family requires the investigator to be able to differentiate between them. Many of the individual family members, such as V$\beta$ 13.1 and V$\beta$ 13.2 differ by only a few amino acids, however, making differentiation extremely difficult.

Antibodies, monoclonal antibodies in particular, are known for their ability to bind to specific protein molecules, allowing differentiation between even very closely related proteins. Differentiation of alternate or variant forms of oncogene proteins, glycoprotein hormones, and even V$\beta$ elements using monoclonal antibodies is known to the art. In the case of V$\beta$ elements, however, very few hybridomas are known which produce the desired mAbs, and those which are known are generally unstable. Since it is known that there are well over 30 different forms of Vβ elements already known (see Kappler et al., supra), and one can expect this number to increase, it is important to have a method available which will generate the desired monoclonal antibodies.

The standard approach to the generation of monoclonal antibodies is essentially that first described by Köhler and Milstein, Nature 256: 495–497 (1975). Essentially, this methodology involves immunizing a subject animal, generally a mouse, rat or rodent with the material against which the antibodies are desired. The recipient's immune system generates antibodies against the material (the "immunogen") via its B cells. These are localized in the animal's spleen. The spleen is removed and treated to separate it into individual cells. Following this, the cells are fused with cell lines which are immortal in culture, generally myeloma cells, in the presence of an agent which facilitates fusion, generally polyethylene glycol. Successful fusions yield hybridomas. Not all of the hybridomas will produce the desired antibody, and it then becomes necessary to screen the hybridomas by assaying them, generally with the antigen in question, to determine their specificity. Since the hybridomas produce only one form of antibody, these are referred to as monoclonal antibodies being, the antibodies derived from a single clone.

Critical for the generation of an antibody response is the recognition by the host animal of the immunogen as foreign. A host's immune system will not respond to a molecule recognized as being identical or very similar to one of its own molecules, under normal conditions. It is well recognized that the human and mouse immune systems are very similar, and generation of human specific antibodies is therefore more difficult than usual when immune receptor molecules are involved.

In the case of T-cell receptors, an additional difficulty exists in that the various members of this family differ to a very small degree, sometimes by less than 20 amino acids. While this degree of difference is key to the mounting of a proper immune response, the small degree of difference may not be sufficient to generate a monoclonal antibody which binds specifically to one member of the family, to the substantial exclusion of others.

Various approaches have been applied in attempting to generate monoclonal antibodies against "difficult" antigens, such as those described supra. Many of these approaches are summarized in Goding, *Monoclonal Antibodies: Principles and Practice* (Academic Press; 1988), the disclosure of which is incorporated by reference, especially pages 1–93. Among the methodologies used are the coupling of the immunogen to a foreign molecule, such as bovine serum albumin, or the use of various adjuvants and other additives which seem to improve the immune response. Such approaches, however, are frequently "hit or miss" and there is little success guaranteed. The art still looks for a systematic approach to this issue.

The early work in monoclonal antibody technology featured the use of whole cells as immunogens. As the field developed, and protocols for purifying individual molecules of interest became more established, protocols in immunology stressed the use of the molecule, rather than the cell. This is because a whole cell features an uncountable array of antigenic sites for generation of antibodies. The investigator's chance of securing an antibody to a particular molecule is remote.

SUMMARY OF THE INVENTION

It has now been found, quite surprisingly, that monoclonal antibodies can be generated against specific components of T-cell receptors using a protocol involving immunization with a whole cell, purified T cell receptor or fragments of a TCR containing the desired component. More specifically, the whole cell is from the same species as the recipient animal, but has been transfected with chimeric DNA. The chimeric DNA codes for a T cell receptor indigenous to the host animal except for a small section, such as a Vα or Vβ molecule, which corresponds to the human form. Surprisingly, in view of the minuscule differences between the immunizing cells and the host cells as well as the similarity of the two immune systems, the host generates antibodies specific to the human element of the molecule and the antibody producing B cells can be used to generate monoclonal antibodies against this element.

DETAILED DESCRIPTION OF PREFERRED EMBODIMENTS

Figure 1:
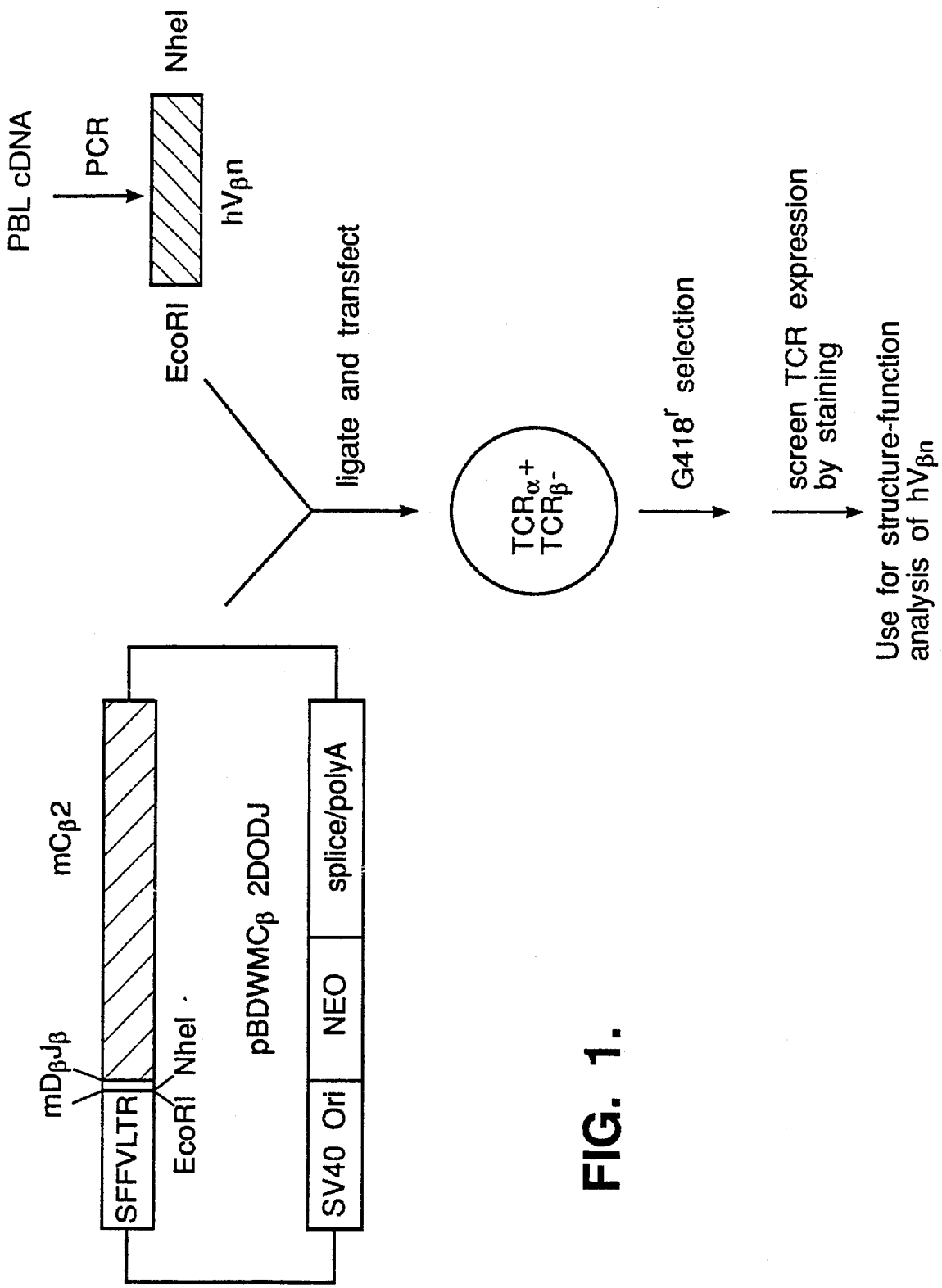
FIGURE 1 shows, schematically, the methodology for expression of human Vβ elements ("hVβ" hereafter) on murine T-cell hybridomas.

Several steps are required in the practice of this invention, as can be gathered from the scheme set forth in FIGURE 1. First, a human gene, in this case a Vβ gene, is introduced into a gene which codes for a mouse T cell receptor ("TCR" hereafter). The resulting recombinant DNA is introduced into a T cell hybridoma. Expression and presentation of the resulting chimera is tested by studying the ability of the hybridoma to produce interleukin-2 ("IL-2") when stimulated by toxins presented by MHC-II molecules. This can also be accomplished by observing reaction with specific antibodies, as described infra. If the transfected cell expresses the chimera, it is then used in an immunization protocol, following Köhler & Milstein, to result in seropositive recipient mice. The spleens of these mice are then used, as outlined supra, in the generation of hybridomas and monoclonal antibodies against the human molecule portion of the chimera.

The experimental details follow.

EXAMPLE 1

An expression vector was constructed which carried mouse Cβ2 and DβJβ elements. This vector is referred to as p BDWMCβ2DODJ hereafter. A human Vβ region was prepared via amplification of cDNA prepared from human PBLS stimulated by anti-CD3 antibody, following Choi et al., Proc. Natl. Acad. Sci. 86: 8941–8945 (1989), the disclosure of which is incorporated by reference herein. The amplified region was joined to the aforementioned vector in a proper reading frame alignment, and was transfected into mouse T cell hybridoma DS23-27.4. This cell line is characterized by expression of all components of the TCR except the β chain. The transfected cells were selected via G418 resistance, as the expression vector also confers resistance to the antibiotic on the transfectants. Expression of the chimeric molecule was determined via screening with either of anti-CD3 (145-2C11) or anti-αβ TCR (H57-597) antibody, as described by Kubo et al., J. Immunol. 142: 2736–2742 (1989), and Leo et al., Proc. Natl. Acad. Sci. USA 84: 1374–1378 (1987). To be more specific as to the amplification, transfection, and other steps, the hVβ elements used were hVβ 13.1 and hVβ 13.2. The cDNA for these elements was prepared following Choi et al., Supra. They were primed and amplified using primers:
5'-GGGAATTCAAGATGGCCATCGCCTCCT-GTGCTGTGC-3' (SEQ ID NO:1)
5'-TAACTGCTAGCACAGAAGTACACAGATGTC-3' (SEQ ID NO:2) for hVβ13.1, and
5'-GGGAATTCAAGATGGCCCTCGGGCTCCT-GTGCTGTGG-3' (SEQ ID NO:3)
5'-GCTGCTAGCACAGAAGTACACAGATGTT-3' for hVβ13.2. (SEQ ID NO:4)
These are primers for polymerase chain reaction amplification as described by Saiki et al., Science 239: 487–491 (1988). Following amplification, the hVβ fragments were subcloned into pTZ18R vector, sequenced, and ligated into the aforementioned vector. This vector contained DβJβCβ2 cDNA obtained from mouse hybridoma DO11.10 described in Blackman et al., Cell 47: 349–357 (1986) ligated into PSFFVSVneo. The vector was transfected into the cells using electroporation following Burgett et al., J. Exp. Med. 170: 1887–1904 (1989), the disclosure of which is incorporated by reference herein. Transfectants were selected with 700 ug/ml G418. The products are designated as either hVβ 13.1, hVβ 13.2, or hVβ 13.1 D2, the last containing portions of both hVβ elements. It was derived by joining 5' hVβ 13.1 sequences to 3' of hVβ 13.2 at amino acid position 66, using the joining primer:
5'-GAAATTCTGTTTTTTTAATGGGAGACAT-TGTAGCC-3' (SEQ ID NO:5)
as described by Ho et al., Gene 77: 51–59 (1989). The rationale for this construct is set forth following the examples.

EXAMPLE 2

As indicated in Example 1, the transfected T cell hybridomas were tested for their ability to respond to presented antigens, via measurement of IL-2 production. Nine different $S.$ $aureus$ toxins presented by murine $H-2^d$ B cell lymphoma A20-11.1 or immobilized antibody H57-597 were used. The toxins were used in concentrations of 10 ug/ml for SEB, SEC1, SEC2, SEC3, and SEA, and 1 ug/ml for SEA, ExT and TSST-1. The results are presented in Table 1, which follows. The # sign indicates less than 10 units of IL-2 per ml were produced, which is the limit of detection for the system. TCR receptor density, which is a measure of surface expression, is presented as mean fluorescence of T cells stained with biotinylated anti-αβTCR H57-597 plus phycoerythrin-streptavidin.

TABLE 1

Response of Transfected T hybridomas to S. Aureus Toxins.

| Vβ Transfected T cell Hybridoma | αβ TCR density | Units/ml IL-2 Produced In Response to A20-11.1 + S. aureus Toxins | | | | | | | | | |
|---|---|---|---|---|---|---|---|---|---|---|---|
| | | None | SEA | SEB | SEC1 | SEC2 | SEC3 | SED | SEE | ExT | TSST-1 | Anti-TCR |
| hVβ13.1-1 | 34 | —# | — | — | — | — | — | — | — | — | — | 843 |
| hVβ13.2-1 | 19 | — | — | — | — | 86 | 44 | — | — | — | — | 256 |
| hVβ13.1D2-1 | 30 | — | — | — | — | 678 | 200 | — | — | — | — | 725 |

These results are consistent with the recognized specificity of hVβ 13.2 and hVβ 13.1 to various $S.$ $aureus$ antigens, showing that the transfectants were expressing chimeric cell surface TCRs.

EXAMPLE 3

Additional experiments were carried out using representative clones tested for reactivity with murine splenic class II+, non T-cells, which had various H-2 haplotypes. The protocol was the same as in Example 2, except for the presenting cells. Spleen cells were prepared by treatment with anti-T serum, followed by treatment with guinea pig complement and irradiation with 1000R. The results represent data where background IL-2 production from toxin depleted cells, which ranged from 10–60 units/ml, was substrated from that obtained with T cell hybridomas present.

Again, a thatch mark indicates that less than 20 units of IL-2/ml were present.

Table 2 presents the data:

TABLE 2

Toxin Presentation is Not MHC Class II Allele Specific

| Antigen Presenting Cells | T cells | Units/ml IL-2 Produced in Response to S. aureus Toxins | | | | | | |
|---|---|---|---|---|---|---|---|---|
| | | none | SEA | SEB | SEC1 | SEC2 | SEC3 | SED |
| B10.A(5R) (IA$^b$IE$^b$)* | hVβ13.1-1 | —# | — | — | — | — | — | — |
| | hVβ13.2-1 | — | — | — | — | 567 | 389 | — |
| | hVβ13.1D2-1 | — | — | — | — | 712 | 311 | 26 |
| B10.BR (IA$^k$IE$^k$) | hVβ13.1-1 | — | — | — | — | — | — | — |
| | hVβ13.2-1 | — | — | — | — | 138 | 99 | — |
| | hVβ13.1D2-1 | — | — | — | — | 540 | 167 | — |
| B10.D2 (IA$^d$IE$^d$) | hVβ13.1-1 | — | — | — | — | — | — | — |
| | hVβ13.2-1 | — | — | — | — | 529 | 246 | — |
| | hVβ13.1D2-1 | — | — | — | — | 1610 | 730 | — |
| B10.Q | hVβ13.1-1 | — | — | — | — | — | — | — |

TABLE 2-continued

Toxin Presentation is Not MHC Class II Allele Specific

| Antigen Presenting Cells | T cells | Units/ml IL-2 Produced in Response to S. aureus Toxins | | | | | | |
|---|---|---|---|---|---|---|---|---|
| | | none | SEA | SEB | SEC1 | SEC2 | SEC3 | SED |
| (IAq) | hVβ13.2-1 | — | — | — | — | 186 | 79 | — |
| | hVβ13.1D2-1 | — | 41 | — | — | 3013 | 1729 | — |
| B10.HTT | hVβ13.1-1 | — | — | — | — | — | — | — |
| (IAsIEs) | hVβ13.2-1 | — | 45 | — | — | 363 | 418 | 22 |
| | hVβ13.1D2-1 | — | 76 | — | 36 | 4975 | 1814 | 74 |

In both examples 2 and 3, as can be seen, Vβ 13.1 bearing transfectants did not respond very well to toxin antigens, but did respond to immobilized anti-Cβ antibody. On the other hand, Vβ 13.2 transfectant did respond to SEC2, and somewhat less well to SEC3, presenting cell being irrelevant. While not shown, these results were consistent over different concentrations.

The results in examples 2 and 3 establish several points. First, human/murine chimeric β chains assembled properly with murine α chains and murine CD3 yield functional receptors. The specifics of the human element of the chimeras were consistent with the results found with normal T cell receptors. A final, and extremely interesting point established by these data is that the T cells bearing both Vβ 13.1 and Vβ 13.2 responded differently to SEC 2 and SEC 3 regardless of the allelic form of murine class II used in the presentation, suggesting that the residues which differ between these two Vβs are involved in toxin, rather than MHC interaction. This augments the observations of White et al., Cell 56: 27–35 (1989) that with respect to an individual TCR, interaction with the allelic residues in the MHC portion of the toxin/MHC ligand can influence the degree of response.

The introduction of the 8 amino acids from positions 67–77 of human Vβ 13.1, yielding hVβ 13.1D2 was sufficient to confer toxin reactivity of Vβ 13.1 to Vβ 13.2, suggesting the site for toxin binding on Vβ lies on this portion of the molecule, but not the face containing CDRs thought to control conventional peptide antigen recognition.

As the data show, this transfectant showed the same panel reactivity as did Vβ 13.2. Magnitudes were actually higher, even when using anti-Cβ as stimulant. Probably, this is due to higher receptor density on the mosaic Vβ transfectant as compared to other cell lines.

EXAMPLE 4

The transfected T cell hybridomas which express hVβ 13.1, hVβ 13.2 and hVβ 13.1 D2 also serve as immunogens for the development of monoclonal antibodies against the human portion thereof. Specifically, immunization and fusion following Köhler & Milstein was followed, yielding sero-positive animals, and then hybridomas which produced monoclonal antibodies which specifically bind to the human portion.

The disclosure thus teaches a vector useful in producing a chimeric T cell receptor molecule, wherein all but a specific portion thereof, such as Vα or Vβ, is of one type, such as murine, whereas the chimeric portion is human. These chimeric molecules are shown to function as normal T cell receptors. In addition, the disclosure teaches the production of transformed T cell hybridoma cell lines which express the foregoing chimeric T cell receptors on their surface. Such T cell hybridomas can be used, e.g., to assay for specific antigens to which they react by measuring, e.g., generation of IL-2 when the transformed cells are contacted with the antigen presented on an MHC II molecule bearing cell. In addition, the disclosure teaches a method of producing antibodies specific to a human T cell receptor element, such as Vβ or Vα, by immunizing an animal with the foregoing transformed cell, followed by fusion with an agent such as myeloma to produce hybridomas, after which screening is carried out to identify salient monoclonal antibodies. Other features of the invention will be apparent to the skilled artisan and shall not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A process for producing a monoclonal antibody which specifically binds to a human T cell Vβ element, comprising:
   (i) transfecting a T cell hybridoma cell, said cell not expressing the T cell receptor β-chain, with a chimeric DNA molecule, said DNA molecule comprising a nucleic acid sequence encoding a human Vβ element and non-human nucleic acid sequences coding for the remaining elements of the T cell receptor β chain, wherein said transfected cell expresses a chimeric T cell receptor;
   (ii) immunizing a non-human animal with the transfected cell, under conditions favoring production of antibodies to said transformed cell, said non-human animal being the same species as said non-human nucleic acid sequences of said DNA molecule;
   (iii) isolating antibody producing cells from said animal;
   (iv) fusing said antibody producing cells with an agent to produce immortal, antibody-producing cells; and
   (v) screening said immortal, antibody-producing cells to isolate antibodies specific to said human T cell Vβ element.

2. The process of claim 1, wherein said non-human animal is a mouse.

3. The process of claim 1, wherein said agent is a myeloma cell.

4. A recombinant DNA vector comprising a gene encoding a chimeric T cell receptor β chain comprised of a human T cell Vβ element, wherein the genes encoding the remaining T cell receptor elements are derived from a single non-human animal, said human and non-human elements arranged in an operable fashion.

5. A non-human T cell hybridoma cell line transfected by the DNA vector of claim 4, said cell line not expressing the β-chain of the T cell receptor and said cell line being derived from the same non-human animal species as the non-human animal portion of said chimeric T cell receptor.

6. The transfected cell line of claim 5, wherein said non-human animal is a mouse.

7. The process of claim 1, wherein said Vβ element is Vβ13.1 or Vβ13.2.

8. The recombinant DNA vector of claim 7, wherein said Vβ element is Vβ13.1 or Vβ13.2.

* * * * *